US007008935B2

(12) United States Patent
Richard et al.

(10) Patent No.: US 7,008,935 B2
(45) Date of Patent: Mar. 7, 2006

(54) AMINE, AMIDE, SULPHONAMIDE AND CARBAMATE DERIVATIVES OF BENZALMALONIC SALTS AND PHOTOPROTECTIVE COSMETIC COMPOSITIONS COMPRISED THEREOF

(75) Inventors: Hervé Richard, Villepinte (FR); Bernadette Luppi, Mitry Mory (FR)

(73) Assignee: L'oreal, Paris (FR)

( * ) Notice: Subject to any disclaimer, the term of this patent is extended or adjusted under 35 U.S.C. 154(b) by 0 days.

(21) Appl. No.: 10/787,759

(22) Filed: Feb. 27, 2004

(65) Prior Publication Data

US 2004/0198977 A1 Oct. 7, 2004

Related U.S. Application Data

(60) Provisional application No. 60/483,652, filed on Jul. 1, 2003.

(30) Foreign Application Priority Data

Mar. 3, 2003 (FR) .................................. 03 02561

(51) Int. Cl.
*A61K 31/194* (2006.01)
*A61K 31/195* (2006.01)
*A61K 7/035* (2006.01)
*A61K 7/02* (2006.01)

(52) U.S. Cl. ................ 514/60; 514/70.9; 514/78.03; 546/184; 562/54; 562/55; 562/76; 562/82

(58) Field of Classification Search ................ 562/54, 562/55, 76, 82; 546/184; 514/60, 70.9, 514/78.03
See application file for complete search history.

(56) References Cited

U.S. PATENT DOCUMENTS

| | | | | |
|---|---|---|---|---|
| 3,706,700 A | * | 12/1972 | Kirchmayer et al. | ........ 252/589 |
| 3,824,273 A | * | 7/1974 | Kirchmayer et al. | .......... 560/55 |
| 3,928,324 A | | 12/1975 | Rosati | |
| 5,849,909 A | * | 12/1998 | Richard et al. | ............. 544/197 |
| 5,985,925 A | * | 11/1999 | Josso et al. | ................. 514/557 |

FOREIGN PATENT DOCUMENTS

| | | |
|---|---|---|
| EP | 0 507 691 A1 | 10/1992 |
| FR | 1 487 593 | 7/1967 |

OTHER PUBLICATIONS

Photochemical Study, L Douarre et al. 1995.*
French Search Report Corresponding to FR 03/02561 Issued on Nov. 7, 2003, 2 pages.

* cited by examiner

*Primary Examiner*—Rita Desai
(74) *Attorney, Agent, or Firm*—Buchanan Ingersoll, P.C.

(57) ABSTRACT

Stable, topically applicable cosmetic/dermatological sunscreen compositions, well suited for the UV-photoprotection of human skin/keratinous materials, contain a thus effective amount of at least one novel amine, amide, sulphonamide or carbamate substituted benzalmalonic salt compound.

21 Claims, No Drawings

AMINE, AMIDE, SULPHONAMIDE AND CARBAMATE DERIVATIVES OF BENZALMALONIC SALTS AND PHOTOPROTECTIVE COSMETIC COMPOSITIONS COMPRISED THEREOF

CROSS-REFERENCE TO PRIORITY/PROVISIONAL APPLICATIONS

This application claims priority under 35 U.S.C. § 119 of FR-03/02561, filed Mar. 3, 2003, and of provisional application Ser. No. 60/483,652, filed Jul. 1, 2003, both hereby expressly incorporated by reference and both assigned to the assignee hereof.

CROSS-REFERENCE TO COMPANION APPLICATION

Our application Ser. No. 10/787,940, filed concurrently herewith and also assigned to the assignee hereof.

BACKGROUND OF THE INVENTION

1. Technical Field of the Invention

The present invention relates to photoprotective compositions comprising amine, amide, sulphonamide and carbamate substituted benzalmalonic salts as sunscreens which are active in the UV radiation region.

The present invention also relates to novel amine, amide, sulphonamide and carbamate derivatives of benzalmalonic salts and to the various applications thereof.

2. Description of Background and/or Related and/or Prior Art

It is known that radiation with wavelengths between 280 nm and 400 nm allows browning of the human epidermis and that radiation with wavelengths between 280 nm and 320 nm, known as UV-B radiation, gives rise to erythema and skin burns which may be detrimental to the development of a natural tan. For these reasons and also for aesthetic reasons there is increasing demand for means of controlling this natural tanning. It is therefore advisable to screen this UV-B radiation.

It is also known that UV-A rays with wavelengths between 320 nm and 400 nm, which cause browning of the skin, are capable of inducing its impairment, particularly in the case of skin which is sensitive and/or continually exposed to sunlight. UV-A rays give rise in particular to a loss of elasticity in the skin and to the appearance of wrinkles, leading to premature skin aging. They promote the triggering of the erythemal reaction or amplify this reaction in certain individuals, and may even be the origin of phototoxic or photoallergic reactions. Consequently, for aesthetic and cosmetic reasons, such as the preservation of the natural elasticity of the skin, increasing numbers of individuals wish to control the effect of UV-A rays on their skin.

Organic sunscreens are usually formulated in compositions which are in the form of oil-in-water or water-in-oil emulsions. Organic sunscreens, which are generally lipophilic or hydrophilic, are present in solution in one or the other of these phases in amounts appropriate to provide the desired sun protection factor (SPF).

The sun protection factor is the ratio of the irradiation time required for the erythema-forming threshold to be reached in the presence of the screen under test to the irradiation time required for this same threshold to be reached in the absence of the screen.

In addition to their capacity to screen sunlight, the photoprotective compounds must also have good cosmetic properties, effective solubility in customary solvents, and especially in aqueous media, and satisfactory photostability.

SUMMARY OF THE INVENTION

A novel class of amine, amide, sulphonamide and carbamate derivatives of benzalmalonic salts has now been developed, having properties of absorbing within the region of UV-B radiation. These compounds can be incorporated into cosmetic formulations. They exhibit good solubility in aqueous media and good photostability and exhibit satisfactory cosmetic qualities.

The present invention thus features novel amine, amide, sulphonamide and carbamate derivatives of benzalmalonic salts, corresponding to formula (1) or (2) below, which will later be more fully described.

This invention likewise features cosmetic or dermatological compositions, suited for the photoprotection of human skin and keratin materials, comprising, in a cosmetically acceptable medium, at least one compound of formula (1) or (2).

Further aspects of the invention will appear from the description which follows.

DETAILED DESCRIPTION OF BEST MODE AND SPECIFIC/PREFERRED EMBODIMENTS OF THE INVENTION

The compounds according to the present invention have the following general formula (1) or (2):

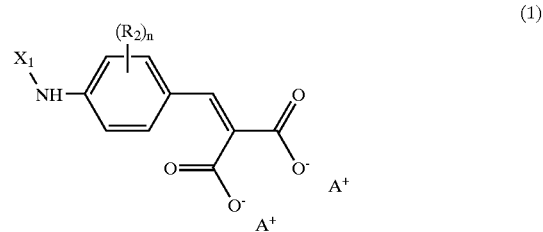

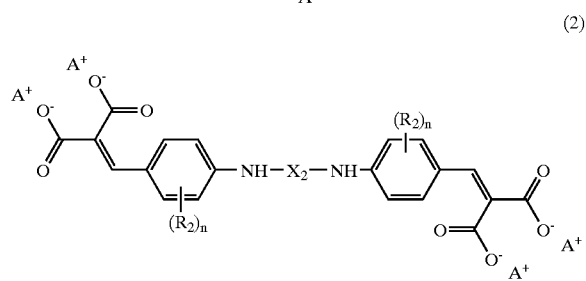

in which $X_1$ is hydrogen or a radical $R_3$—(C=O)—, $R_3$—$SO_2$— or $R_3$—O—(C=O)—; $X_2$ is a divalent radical of formula —(C=O)—$R'_3$—(C=O)—, —$SO_2$—$R'_3$—$SO_2$— or —(C=O)—O—$R'_3$—O—(C=O)—; $R_2$ is a linear or branched $C_{1-8}$ alkyl radical; n is 0, 1 or 2; $R_3$ is a linear or branched $C_1$–$C_{30}$ alkyl radical or $C_3$–$C_{30}$ alkenyl radical, optionally bearing one or more hydroxyl substituents and optionally containing in the hydrocarbon chain one or more heteroatoms selected from among oxygen, nitrogen and silicon atoms, or an optionally substituted $C_6$–$C_{20}$ aryl radical; $R'_3$ is a single valence bond or a linear or branched divalent $C_1$–$C_{30}$ alkylene or $C_3$–$C_{30}$ alkenylene radical, optionally bearing one or more hydroxyl substituents and optionally containing in the hydrocarbon chain one or more heteroatoms selected from among oxygen, nitrogen and silicon atoms; and the radicals A, which may be identical or different, are each a cation of the alkali metal type such as sodium or potassium, an ammonium group, a $C_1$–$C_{20}$ mono-, di- or trialkylammonium radical, a $C_2$–$C_{20}$ mono-, di- or trialkanolammonium radical, or a $C_5$–$C_8$ quaternary nitrogen-containing heterocyclic ring member.

In the formula (I) above, the alkyl radicals may be selected in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The particularly preferred alkyl radical is the methyl radical.

In the formulae (I) above, the alkoxy radicals may be selected in particular from methoxy, ethoxy, n-propoxy, isopropoxy, n-butoxy and isobutoxy radicals. The particularly preferred alkoxy radical is the methoxy radical.

In the formula (I) above, the alkenyl radicals may be selected in particular from propylene and butene radicals.

In the formula (I) above, the aryl radicals are, for example, benzyl or phenyl.

In the formula (I) above, the $C_1$–$C_{20}$ mono-, di- or trialkylammonium radicals may be selected in particular from mono-, di- and trimethylammonium and mono-, di- and triethylammonium.

In the formula (I) above, the $C_2$–$C_{20}$ mono-, di- or trialkanolammonium radicals may be selected in particular from mono-, di- and triethanolammonium.

In the formula (I) above, the quaternary heterocyclic ring members may be selected in particular from piperidinium, morpholinium, pyrrolidinium and pyrrolinium.

Among the compounds of formula (I) mention will be made more particularly still of those of formula (I) for which:
$X_1$ is hydrogen or $R_3$—(C=O)—;
n=0;
$R_3$ is an alkyl radical; and
A is an alkali metal or a piperidinium group.

Among the compounds of formula (I) mention will be made more particularly still of those selected from:

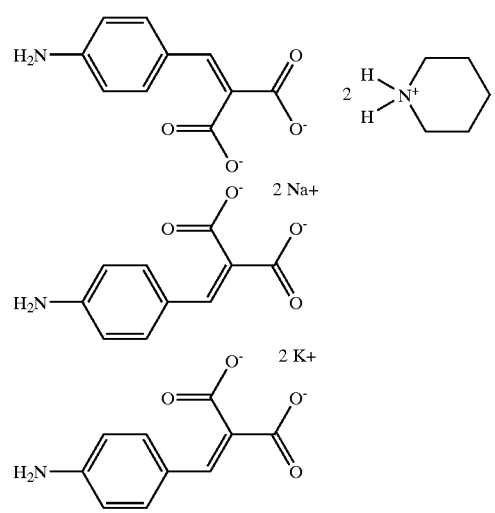

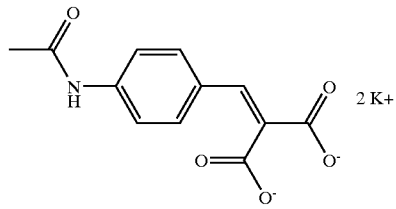

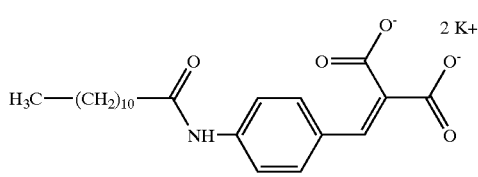

The amide, sulphonamide and carbamate derivatives of the salts of benzalmalonic acid of formula (1) may be obtained by the following two synthesis pathways:

Pathway A: preparation of amide, sulphonamide and carbamate derivatives by condensing para-aminobenzaldehyde (3) with the corresponding acid chlorides, sulphochlorides and chloroformates (4) in accordance with scheme (I) below:

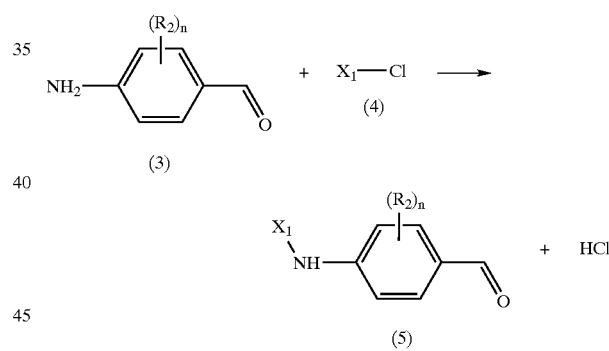

followed by condensation of the benzaldehyde (5) with the di-salt of malonic acid in accordance with scheme (II) below:

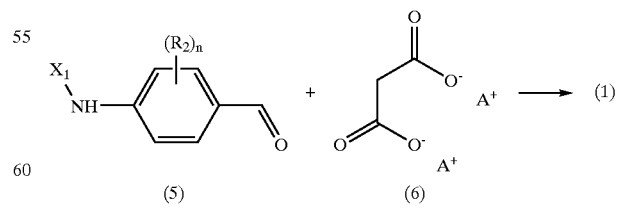

Pathway B: preparation of the di-salt of para-aminobenzalmalonic acid (6) by condensation of para-aminobenzaldehyde (3) with the di-salt of malonic acid (6) in accordance with scheme (III) below:

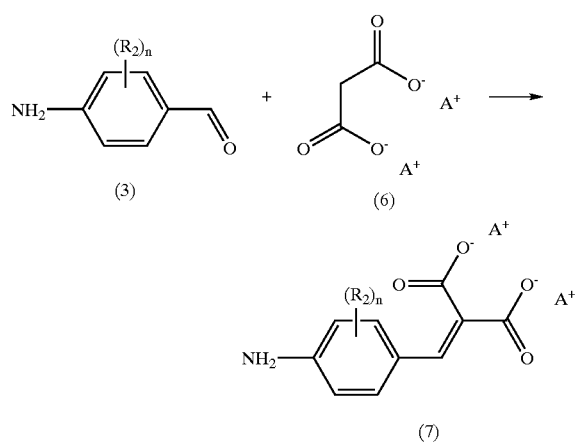

followed by the reaction of the salts of para-aminobenzalmalonic acid with the corresponding acid chlorides, sulphochlorides and chloroformates in accordance with scheme (IV) below:

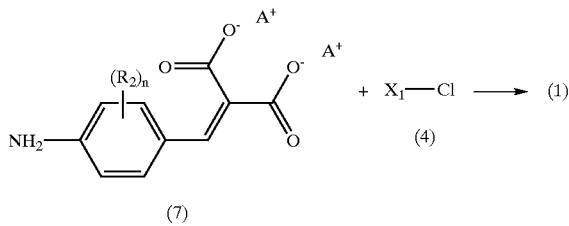

The present invention further provides for the new direct synthesis of the salts of para-aminomalonic acid by the process depicted by scheme (III) above.

This synthesis is generally effected without solvent or in the presence of an alcoholic solvent such as methanol, ethanol or isopropyl alcohol and at a temperature of between 40° C. and 120° C. and more particularly between 60° C. and 95° C.

The compounds of formula (I) are generally present in the composition of the invention in proportions of between 0.01% and 20% by weight, preferably between 0.1% and 10% by weight, relative to the total weight of the composition.

The compositions according to the invention may further comprise other, complementary organic or inorganic UV screens which are active in UVA and/or UVB ranges and which are water-soluble or fat-soluble or else are insoluble in the cosmetic solvents commonly employed.

The complementary organic sunscreens are selected in particular from anthranilates; cinnamic derivatives; dibenzoylmethane derivatives; salicylic derivatives; camphor derivatives; triazine derivatives, such as those described in U.S. Pat. No. 4,367,390, EP-863,145, EP-517,104, EP-570, 838, EP-796,851, EP-775,698, EP-878,469, EP-933,376, EP-507,691, EP-507,692, EP-790,243, EP-944,624; benzophenone derivatives; β,β-diphenylacrylate derivatives; benzotriazole derivatives; benzalmalonate derivatives; benzimidazole derivatives; imidazolines; bis-benzazolyl derivatives as described in EP-669,323 and U.S. Pat. No. 2,463, 264; p-aminobenzoic acid (PABA) derivatives; methylenebis(hydroxyphenylbenzotriazole) derivatives, as described in U.S. Pat. Nos. 5,237,071, 5,166,355, GB-2-303,549, DE-1-9-726,184 and EP-893,119; polymer screens and silicone screens, such as those described in particular in WO 93/04665; dimers derived from α-alkylstyrene, such as those described in DE-1-9-855,649; 4,4-diarylbutadienes as described in EP-0-967,200, DE-1-9-746,654, DE-1-9-755, 649, EP-A-1-008,586, EP-1-133,980 and EP-1-133,981, and mixtures thereof.

As examples of complementary organic sunscreens mention may be made of those denoted below by their INCI name:

para-Aminobenzoic Acid Derivatives:
PABA,
Ethyl PABA,
Ethyl Dihydroxypropyl PABA,
Ethylhexyl Dimethyl PABA, sold in particular under the name Escalol 507 by ISP,
Glyceryl PABA,
PEG-25 PABA, sold under the name Uvinul P25 by BASF.
Salicylic Derivatives:
Homosalate, sold under the name Eusolex HMS by Rona/EM Industries,
Ethylhexyl Salicylate, sold under the name Neo Heliopan OS by Haarmann and Reimer,
Dipropylene glycol salicylate, sold under the name Dipsal by Scher,
TEA Salicylate, sold under the name Neo Heliopan TS by Haarmann and Reimer.
Dibenzoylmethane Derivatives:
Butyl methoxydibenzoylmethane, sold in particular under the trademark Parsol 1789 by Hoffmann La Roche,
Isopropyl Dibenzoylmethane.
Cinnamic Derivatives:
Ethylhexyl methoxycinnamate, sold in particular under the trademark Parsol MCX by Hoffmann La Roche,
Isopropyl Methoxycinnamate,
Isoamyl Methoxycinnamate, sold under the trademark Neo Heliopan E 1000 by Haarmann and Reimer,
Cinoxate,
DEA Methoxycinnamate,
Diisopropyl Methylcinnamate,
Glyceryl Ethylhexanoate Dimethoxycinnamate.
β,β'-Diphenylacrylate Derivatives:
Octocrylene, sold in particular under the trademark Uvinul N539 by BASF,
Etocrylene, sold in particular under the trademark Uvinul N35 by BASF.
Benzophenone Derivatives:
Benzophenone-1, sold under the trademark Uvinul 400 by BASF,
Benzophenone-2, sold under the trademark Uvinul D50 by BASF,
Benzophenone-3 or oxybenzone, sold under the trademark Uvinul M40 by BASF,
Benzophenone-4, sold under the trademark Uvinul MS40 by BASF,
Benzophenone-5,
Benzophenone-6, sold under the trademark Helisorb 11 by Norquay,
Benzophenone-8, sold under the trademark Spectra-Sorb UV-24 by American Cyanamid,
Benzophenone-9, sold under the trademark Uvinul DS-49 by BASF,
Benzophenone-12
n-hexyl 2-(4-diethylamino-2-hydroxybenzoyl)benzoate.
Benzylidenecamphor Derivatives:

3-Benzylidene camphor, manufactured under the name Mexoryl SD by Chimex,

4-Methylbenzylidene camphor, sold under the name Eusolex 6300 by Merck,

Benzylidene Camphor Sulphonic Acid, manufactured under the name Mexoryl SL by Chimex, Camphor Benzalkonium Methosulphate, manufactured under the name Mexoryl SO by Chimex, Terephthalylidene Dicamphor Sulphonic Acid, manufactured under the name Mexoryl SX by Chimex, Polyacrylamidomethyl Benzylidene Camphor, manufactured under the name Mexoryl SW by Chimex.

Phenylbenzimidazole Derivatives:

Phenylbenzimidazole Sulphonic Acid, sold in particular under the trademark Eusolex 232 by Merck, Disodium Phenyl Dibenzimidazole Tetra-sulphonate, sold under the trademark Neo Heliopan AP by Haarmann and Reimer.

Triazine Derivatives:

Anisotriazine, sold under the trademark Tinosorb S by Ciba Geigy,

Ethylhexyl triazone, sold in particular under the trademark Uvinul T150 by BASF, 2,4,6-tris(diisobutyl 4'-aminobenzalmalonate)-s-triazine, Diethylhexyl Butamido Triazone, sold under the trademark Uvasorb Heb by Sigma 3V.

Phenylbenzotriazole Derivatives:

Drometrizole Trisiloxane, sold under the name Silatrizole by Rhodia Chimie,

Methylene bis-Benzotriazolyl Tetramethylbutylphenol, sold in solid form under the trademark Mixxim BB/100 by Fairmount Chemical or in micronized form in aqueous dispersion under the trademark Tinosorb M by Ciba Specialty Chemicals.

Anthranilic Derivatives:

Menthyl anthranilate, sold under the trademark Neo Heliopan MA by Haarmann and Reimer.

Imidazoline Derivatives:

Ethylhexyl Dimethoxybenzylidene Dioxoimidazoline Propionate.

Benzalmalonate Derivatives:

Polyorganosiloxane containing benzalmalonate functions sold under the trademark Parsol SLX by Hoffmann La Roche.

4,4-Diarylbutadiene Derivatives:

1,1-dicarboxy(2,2'-dimethylpropyl)-4,4-diphenylbutadiene and mixtures thereof.

The preferred complementary organic UV screens are selected from:

Ethylhexyl Salicylate,
Ethylhexyl Methoxycinnamate,
Butyl Methoxydibenzoylmethane,
Octocrylene,
Phenylbenzimidazole Sulphonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulphonic Acid,
Disodium Phenyl Dibenzimidazole Tetra-sulphonate,
2,4,6-Tris(diisobutyl 4'-aminobenzalmalonate)-s-triazine,
Anisotriazine,
Ethylhexyl triazone,
Diethylhexyl Butamido Triazone,
Methylene bis-Benzotriazolyl Tetramethylbutylphenol,
Drometrizole Trisiloxane,
1,1-Dicarboxy(2,2'-dimethylpropyl)-4,4-diphenylbutadiene,
and mixtures thereof.

The complementary inorganic sunscreens are selected from pigments, including nanopigments (mean primary particle size: generally between 5 nm and 100 nm, preferably between 10 nm and 50 nm), of coated or uncoated metal oxides, for example nanopigments of titanium oxide (amorphous or crystalline in rutile and/or anatase form), iron oxide, zinc oxide, zirconium oxide or cerium oxide, which are all well-known UV photoprotectants. Conventional coating agents are, moreover, alumina and/or aluminium stearate. Coated or uncoated metal oxide nanopigments of this kind are described in particular in EP-518,772 and EP-518,773.

The complementary UV screens in accordance with the invention are generally present in the compositions according to the invention in proportions ranging from 0.01% to 20% by weight relative to the total weight of the composition, and preferably ranging from 0.1% to 10% by weight relative to the total weight of the composition.

The cosmetic compositions according to the invention may further comprise tanning and/or artificial skin browning agents (self-tanning agents) such as dihydroxyacetone (DHA).

The compositions in accordance with the present invention may further comprise conventional cosmetic adjuvants, selected in particular from fats, organic solvents, ionic and nonionic thickeners, softeners, humectants, antioxidants, moisturizers, desquamating agents, free-radical scavengers, antipollutants, antibacterials, anti-inflammatories, depigmenting agents, propigmenting agents, opacifiers, stabilizers, emollients, silicones, antifoams, insect repellants, perfumes, preservatives, anionic, cationic, nonionic, zwitterionic and amphoteric surfactants, substance P antagonists, substance CGRP antagonists, fillers, pigments, polymers, propellants, alkalifying or acidifying agents or any other ingredient commonly used in the field of cosmetology and/or dermatology.

The fats may be an oil or wax or mixtures thereof. An oil is a compound which is liquid at ambient temperature. A wax is a compound which is solid or substantially solid at ambient temperature and whose melting point is generally above 35° C.

As oils mention may be made of mineral oils (paraffin); vegetable oils (sweet almond oil, macadamia oil, blackcurrant seed oil, jojoba oil); synthetic oils such as perhydrosqualene; fatty alcohols, acids or esters (such as $C_{12}$–$C_{15}$ alcohol benzoate, sold under the trademark Finsolv TN by Witco, octyl palmitate, isopropyl lanolate, and triglycerides, including those of capric/caprylic acids), ethoxylated or propoxylated fatty ethers and esters; silicone oils (cyclomethicone, polydimethylsiloxanes or PDMS) or fluoro oils, and polyalkylenes.

As waxy compounds mention may be made of paraffin, carnauba wax, beeswax and hydrogenated castor oil.

Among organic solvents mention may be made of lower alcohols and polyols. The latter may be selected from glycols and glycol ethers such as ethylene glycol, propylene glycol, butylene glycol, dipropylene glycol and diethylene glycol.

Thickeners may be selected in particular from crosslinked acrylic polymers such as the Carbomer products, crosslinked acrylate/$C_{10}$–$C_{30}$ alkyl acrylate polymers of the Pemulen type, or the polyacrylate-3 sold under the name Viscophobe DB 1000 by Amerchol; polyacrylamides such as the polyacrylamide $C_{13}$–$C_{14}$ isoparaffin and laureth-7 emulsion which is sold under the name Sepigel 305 by SEPPIC, AMPS homopolymers or copolymers such as Hostacerin AMPS, sold by Clariant, modified or non-modified celluloses and guar gums, such as hydroxypropylguar gum, methylhydroxyethylcellulose and hydroxypropylmethylcellulose, xanthan gum, and nanoscale silicas of Aerosil type.

One skilled in this art will to take care to select the optional complementary compound or compounds mentioned above and/or its or their quantities such that the advantageous properties intrinsically attaching to the compounds in accordance with the invention are not, or not substantially, impaired by the intended addition or additions.

The compositions according to the invention can be prepared by techniques which are well known to the person skilled in the art, especially those intended for the preparation of oil-in-water or water-in-oil emulsions.

This composition may be present in particular in the form of a simple or complex emulsion (O/W, W/O, O/W/O or W/O/W) such as a cream or milk, or in the form of a gel or cream gel, in the form of a lotion, an oil, a powder or a solid stick, and may where appropriate be packaged as an aerosol and be present in the form of a foam or spray.

The compositions according to the invention are preferably in the form of an oil-in-water or water-in-oil emulsion.

When the composition is an emulsion its aqueous phase may comprise a nonionic vesicle dispersion prepared by known methods (Bangham, Standish and Watkins, *J. Mol. Biol.*, 13, 238 (1965), FR-2,315,991 and FR-2,416,008).

When the cosmetic composition according to the invention is used for the care of the human epidermis it may be present in suspension or dispersion form in solvents or fats, in the form of a nonionic vesicle dispersion or else in the form of an emulsion, preferably an oil-in-water emulsion, such as a cream or milk, or in the form of an ointment, gel, cream gel, sun oil, solid stick, powder, aerosol foam or spray.

When the cosmetic composition according to the invention is used for the care of the hair it may be present in the form of a shampoo, lotion, gel, emulsion or nonionic vesicle dispersion and may constitute, for example, a rinsing composition, a composition for application before or after shampooing, before or after coloring or bleaching, before, during or after perming or straightening, a styling or treatment lotion or gel, a lotion or a gel for brushing or setting, a perming or straightening composition or a hair coloring or bleaching composition.

When the composition is used as a makeup product for the nails, lips, eyelashes, eyebrows or skin, such as an epidermal treatment cream, foundation, lipstick, eyeshadow, blusher, mascara or liner, also called eyeliner, it may be present in solid or paste form, anhydrous or aqueous, such as oil-in-water or water-in-oil emulsions, nonionic vesicle dispersions or else suspensions.

By way of indication, for the antisun formulations in accordance with the invention which have a vehicle of the oil-in-water emulsion type, the aqueous phase (containing in particular the hydrophilic screens) represents generally from 50% to 95% by weight, preferably from 70% to 90% by weight, relative to the entirety of the formulation, the oily phase (containing in particular the lipophilic screens) from 5% to 50% by weight, preferably from 10% to 30% by weight, relative to the entirety of the formulation, and the (co)emulsifier(s) from 0.5% to 20% by weight, preferably from 2% to 10% by weight, relative to the entirety of the formulation.

The invention further provides for the use of a compound of formula (1) or (2) as defined above in a cosmetic or dermatological composition as a UV radiation screen.

The invention further provides for the use of a compound of formula (1) or (2) as defined above in a cosmetic composition as an agent for controlling the change in the color of the skin brought about by UV radiation.

The invention further provides for the use of a compound of formula (1) or (2) as defined above as a light stabilizer for synthetic polymers such as plastics or glasses, especially spectacle lenses or contact lenses.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Preparation of the Dipiperidinium Salt of 2-(4-aminobenzylidene)malonic Acid

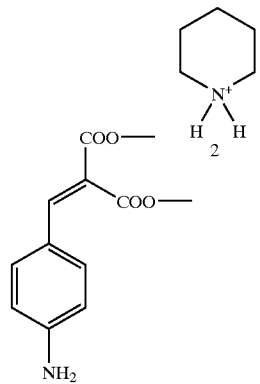

A reactor equipped with a thermometer, a mechanical stirrer and a condenser is charged with piperidine (206.6 g, 2.42 mol). This initial charge is heated to 40° C. Malonic acid is introduced in portions over 15 minutes, without exceeding 70° C. (83.4 g, 0.8 mol). The resulting viscous paste is held at 70° C. and p-aminobenzaldehyde is introduced in portions over 15 minutes (97 g, 0.8 mol). The viscous mixture is left with stirring at 90° C. and the viscosity is monitored. When the viscosity increases, the introduction of isopropyl alcohol is commenced (after 1 hour 15 minutes). 200 ml of isopropyl alcohol are introduced over 2 hours 50 minutes. The mixture is cooled and filtered. The precipitate obtained is washed with a minimal amount of isopropyl alcohol. Drying under vacuum over $P_2O_5$ gives 210 g (yield: 70%) of the product of Example 1 in the form of a yellow powder:

UV (water) $\lambda_{max}$=305 nm $\epsilon_{max}$=16 840 $E_{1\%}$=446

EXAMPLE 2

Preparation of the Disodium Salt of 2-(4-aminobenzylidene)malonic Acid

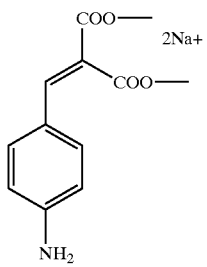

The procedure of Example 1 is repeated until the step of addition of isopropyl alcohol. Subsequently sodium hydroxide (200 ml of 35% strength aqueous sodium hydroxide solution, 1.75 mol) is introduced over 15 minutes at a temperature of 90° C.–70° C., with continued stirring. The mixture is cooled to 40° C. 700 ml of ethanol are added and the reaction mixture is filtered on Frit No. 3. The solid is taken up in at least 500 ml of water and filtered. This gives approximately 5 g of residue, which is discarded. The filtrate is concentrated to half its volume and 700 ml of 95° ethanol are added, and the product is left to crystallize. Filtration and drying under vacuum over $P_2O_5$ give 140 g (yield: 70%) of the product of Example 2 in the form of a yellow powder:

UV (water) $\lambda_{max}$=305 nm $\epsilon_{max}$=16 830 $\mu E_{1\%}$=670

EXAMPLE 3

Preparation of the Dipotassium Salt of 2-(4-aminobenzylidene)malonic Acid

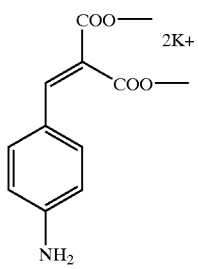

The procedure of Example 1 is repeated until the step of addition of isopropyl alcohol. Then 85% potassium hydroxide (114 g, 1.75 mol) in solution in 200 ml of 96% ethanol is introduced over 15 minutes at a temperature of 90° C.–70° C., with continual stirring. The mixture is cooled to 40° C. 700 ml of 96% ethanol are added and the reaction mixture is filtered on Frit No. 3. The solid is taken up in at least 500 ml of water and filtered. The filtrate is concentrated to half its volume, 500 ml of isopropanol are added, and the product is allowed to crystallize. Filtration and drying under vacuum over $P_2O_5$ give 205 g (yield: 90%) of the product of Example 3 in the form of a light-yellow powder:

UV (Water) $\lambda_{max}$=306 nm $\epsilon_{max}$=14 050 $E_{1\%}$=496

EXAMPLE 4

Preparation of the Dipotassium Salt of 2-(4-acetamidobenzylidene)malonic Acid

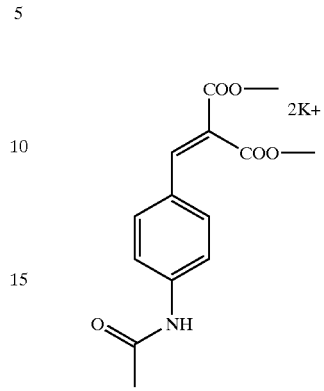

A reactor equipped with a thermometer, a mechanical stirrer and a condenser is charged with piperidine (30 ml). It is heated to 40° C. Malonic acid is introduced in portions over 15 minutes without exceeding 70° C. (10.4 g, 0.1 mol). p-Acetamidobenzaldehyde (16.3 g, 0.1 mol) is introduced in portions. The mixture is left at 95° C. with stirring and with monitoring of the viscosity.

When the viscosity increases, the introduction of isopropyl alcohol is commenced (after 1 hour). 20 ml of isopropyl alcohol are introduced over 1 hour. The mixture is cooled. Potassium (15 g) in solution in 80 ml of 96% ethanol is added. The resulting precipitate is filtered, washed with a minimum amount of 96% ethanol and then dried under vacuum. This gives 27.9 g (yield: 86%) of the product of Example 4 in the form of a white powder:

UV (Water) $\lambda_{max}$=292 nm $\epsilon_{max}$=16 220 $E_{1\%}$=498

EXAMPLE 5

Preparation of the Dipotassium Salt of 2-(4-laurylamidobenzylidene)malonic Acid

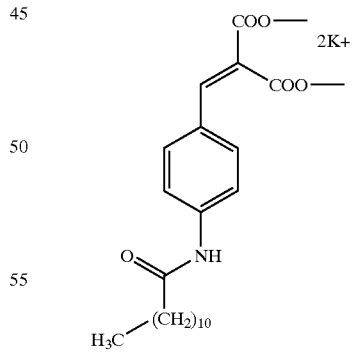

First step: Preparation of para-laurylamidobenzaldehyde:

A reactor equipped with a thermometer, a mechanical stirrer and a condenser is charged with para-aminobenzaldehyde (12.1 g, 0.1 mol) in suspension in 100 ml of 1,2-dichloroethane. Lauroyl chloride (21.8 g, 0.1 mol) is introduced, followed by triethylamine (10.1 g, 0.1 mol). The mixture is heated at 1,2-dichloroethane reflux for 4 hours. It is cooled and the unreacted para-aminobenzaldehyde is filtered off. Following concentration of the filtrate, the residue is chromatographed on silica (eluent $CH_2Cl_2$ then $CH_2Cl_2$/MeOH 95:5) to give 3 g (yield: 10%) of clean fractions of paralaurylamidobenzaldehyde in the form of a white powder, which is used as it is in the following step:

Second step: Preparation of the Derivative of Example 5:

A reactor equipped with a thermometer, a mechanical stirrer and a condenser is charged with piperidine (1 g). It is heated to 40° C. Malonic acid (0.5 g) is introduced. para-Laurylamidobenzaldehyde (1 g, $3 \times 10^{-3}$ mol) and 2 ml of isopropyl alcohol are introduced. The mixture is left with stirring at 90° C. for 2 hours. It is cooled. Potassium (1 g) in solution in 10 ml of 96% ethanol is added. The resulting precipitate is filtered, washed with a minimum amount of 96% ethanol and then dried under vacuum. This gives 0.6 g (yield: 45%) of the product of Example 5 in the form of a white waxy solid:

UV (Water) $\lambda_{max}=292$ nm $\epsilon_{max}=14\ 010$ $E_{1\%}=422$

Example 6

Antisun Composition (Oil-In-Water Emulsion)

| | |
|---|---|
| Compound of Example 4 | 3 g |
| 80/20 mixture of cetylstearyl alcohol and ethoxylated cetylstearyl alcohol (33 EO units) sold by Tensia under the trademark Dehsconet ® 390 | 7 g |
| Mixture of glycerol monostearate and distearate, sold under the trademark Cerasynth ® SD by ISP | 2 g |
| Cetyl alcohol | 1.5 g |
| Polydimethylsiloxane sold under the name DC200Fluid ® by Dow Corning | 1.5 g |
| Glycerol | 15 g |
| Preservatives | qs |
| Demineralized water qs | 100 g |

The fatty phase is heated at approximately 70–80° C. until melting is complete. The aqueous phase, containing the compound of Example 4, is subsequently added in one go at 80° C. with vigorous stirring. Stirring is maintained for 10 to 15 minutes and then the mixture is allowed to cool with moderate stirring, to approximately 40° C., and the preservatives are added. This gives an antisun cream which is particularly effective against UV-B.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

The invention claimed is:

1. An amine, amide, sulphonamide or carbamate substituted benzalmalonic salt compound having the following general formula (1) or (2):

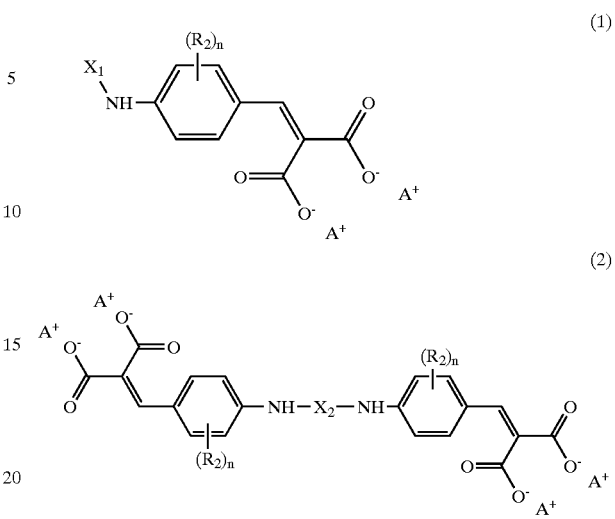

in which $X_1$ is hydrogen or a radical $R_3$—(C=O)—, $R_3$—$SO_2$— or $R_3$—O—(C=O)—; $X_2$ is a divalent radical of formula —(C=O)—$R'_3$—(C=O)—, —$SO_2$—$R'_3$—$SO_2$— or —(C=O)—O—$R'_3$—O—(C=O)—; $R_2$ is a linear or branched $C_{1-8}$ alkyl radical n is 0, 1 or 2; $R_3$ is a linear or branched $C_1$–$C_{30}$ alkyl radical or $C_3$–$C_{30}$ alkenyl radical, optionally bearing one or more hydroxyl substituents and optionally containing in the hydrocarbon chain one or more heteroatoms selected from among oxygen, nitrogen and silicon atoms, or an optionally substituted $C_6$–$C_{20}$ aryl radical; $R'_3$ is a single valence bond or a linear or branched divalent $C_1$–$C_{30}$ alkylene or $C_3$–$C_{30}$ alkenylene radical, optionally bearing one or more hydroxyl substituents and optionally containing in the hydrocarbon chain one or more heteroatoms selected from among oxygen, nitrogen and silicon atoms; and the radicals A, which may be identical or different, are each an alkali metal cation, an ammonium group, a $C_1$–$C_{20}$ mono-, di- or trialkylammonium radical, a $C_2$–$C_{20}$ mono-, di- or trialkanolammonium radical, or a $C_5$–$C_8$ quaternary nitrogen-containing heterocyclic ring member.

2. A benzalmalonic salt compound as defined by claim 1, having the formula (1), wherein $X_1$ is hydrogen or $R_3$—(C=O)—; n=0; $R_3$ is an alkyl radical; and A is an alkali metal or a piperidinium group.

3. A benzalmalonic salt compound as defined by claim 1, having the formula (2).

4. A benzalmalonic salt compound as defined by claim 1, having the formula:

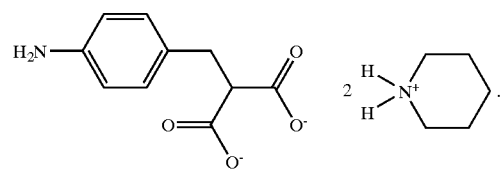

5. A benzalmalonic salt compound as defined by claim 1, having the formula:

6. A benzalmalonic salt compound as defined by claim 1, having the formula:

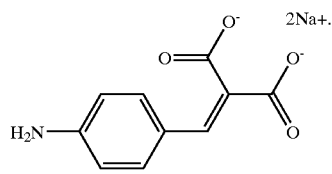

7. A benzalmalonic salt compound as defined by claim 1, having the formula:

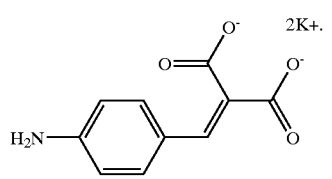

8. A benzalmalonic salt compound as defined by claim 1, having the formula:

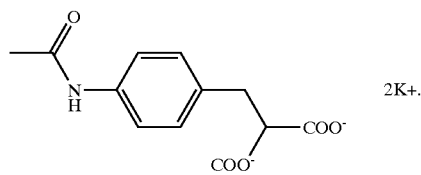

9. A process for the preparation of a compound of formula (1) as defined in claim 1, comprising first obtaining a di-salt of para-aminobenzalmalonic acid (7) by condensation of para-aminobenzaldehyde (3) with the di-salt of malonic acid (6) in accordance with the reaction scheme below:

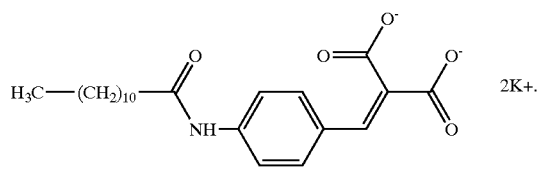

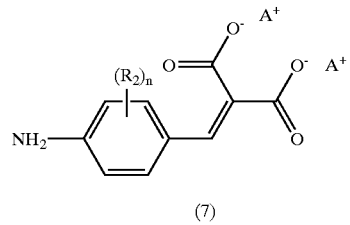

and then, in a second step, reacting the di-salt of para-aminobenzalmalonic acid (7) thus obtained with an acid chloride, sulphochloride or chloroformate of formula (4) in accordance with the scheme below:

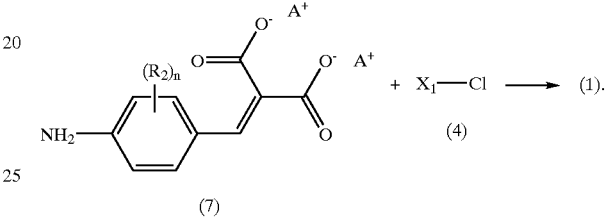

10. The process as defined by claim 9, carried out in the absence of solvent or in the presence of an alcoholic solvent, and at a temperature of between 40° C. and 120° C.

11. A topically applicable cosmetic/dermatological composition suited for the UV-photoprotection of human skin/keratinous materials, comprising an effective UV-photoprotecting amount of at least one amine, amide, sulphonamide or carbamate substituted benzalmalonic salt compound having the following general formula (1) or (2):

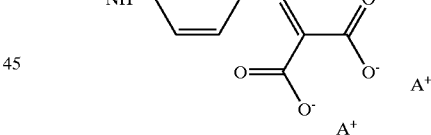

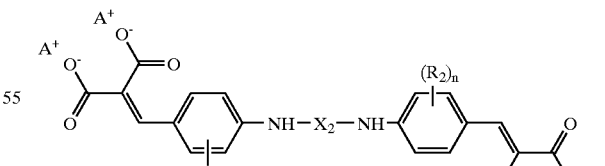

in which $X_1$ is hydrogen or a radical $R_3$—(C=O)—, $R_3$—$SO_2$— or $R_3$—O—(C=O)—; $X_2$ is a divalent radical of formula —(C=O)—$R'_3$—(C=O)—, —$SO_2$—$R'_3$—$SO_2$— or —(C=O)—O—$R'_3$—O—(C=O)—; $R_2$ is a linear or or branched $C_{1-8}$ alkyl radical; n is 0, 1 or 2; $R_3$ is a linear or branched $C_1$–$C_{30}$ alkyl radical or $C_3$–$C_{30}$ alkenyl radical, optionally bearing one or more hydroxyl substituents and optionally containing in the hydrocarbon chain one or more heteroatoms selected from among oxygen, nitrogen and silicon atoms, or an optionally substituted $C_6$–$C_{20}$ aryl radical; $R'_3$ is a single valence bond or a linear or branched divalent $C_1$–$C_{30}$ alkylene or $C_3$–$C_{30}$ alkenylene radical, optionally bearing one or more hydroxyl substituents and optionally containing in the hydrocarbon chain one or more heteroatoms selected from among oxygen, nitrogen and silicon atoms; and the radicals A, which may be identical or different, are each an alkali metal cation, an ammonium group, a $C_1$–$C_{20}$ mono-, di- or trialkylammonium radical, a $C_2$–$C_{20}$ mono-, di- or trialkanolammonium radical, or a $C_s$–$C_8$ quaternary nitrogen-containing heterocyclic ring member, and a topically applicable, cosmetically/dermatologically acceptable medium therefor.

12. The cosmetic/dermatological sunscreen composition as defined by claim 11, said at least one benzalmalonic salt compound having the formula (1), wherein $X_1$ is hydrogen or $R_3$—(C=O)—; n=0; $R_3$ is an alkyl radical; and A is an alkali metal or a piperidinium group.

13. The cosmetic/dermatological sunscreen composition as defined by claim 11, said at least one benzalmalonic salt compound having the formula (2).

14. The cosmetic/dermatological sunscreen composition as defined by claim 11, said at least one benzalmalonic salt compound comprising from 0.01% to 20% by weight thereof.

15. The cosmetic/dermatological sunscreen composition as defined by claim 11, said at least one benzalmalonic salt compound comprising from 0.1% to 10% by weight thereof.

16. The cosmetic/dermatological sunscreen composition as defined by claim 11, comprising an oil-in-water or water-in-oil emulsion.

17. The cosmetic/dermatological sunscreen composition as defined by claim 11, in the form of a nonionic vesicle dispersion, a lotion, a paste, a cream, a milk, a gel, a cream gel, a suspension, an ointment, a dispersion, an oil, a powder, a solid stick, a foam or a spray.

18. The cosmetic/dermatological sunscreen composition as defined by claim 11, in the form of a makeup for the eyelashes, eyebrows, nails or skin.

19. The cosmetic/dermatological sunscreen composition as defined by claim 11, in the form of a shampoo, hair lotion, hair gel, hair emulsion or nonionic vesicle dispersion.

20. A metod for photoprotecting human skin/keratinous materials against the damaging effects of UV-radiation, comprising topically applying thereon a thus effective amount of the cosmetic/dermatological sunscreen composition as defined by claim 11.

21. A method for controlling the change in the color of human skin brought about by exposure to UV-radiation, comprising topically applying thereon a thus effective amount of the cosmetic/dermatological sunscreen composition as defined by claim 11.

* * * * *